United States Patent [19]

Chrithian et al.

[11] Patent Number: 4,852,406

[45] Date of Patent: Aug. 1, 1989

[54] METHOD AND APPARATUS FOR DETERMINING THE COEFFICIENT OF INTERNAL FRICTION OF STEEL OR THE LIKE

[75] Inventors: Oliver Christian, Creil; Charles Brun, Montataire, both of France

[73] Assignee: Usinor Aciers, Puteaux, France

[21] Appl. No.: 72,253

[22] Filed: Jul. 10, 1987

[30] Foreign Application Priority Data

Jul. 11, 1986 [FR] France ................. 86 10214

[51] Int. Cl.$^4$ .................. G01H 11/04; G01H 3/38; G01L 1/14; G01N 27/80
[52] U.S. Cl. ..................... 73/579; 324/209
[58] Field of Search ........... 324/209, 224, 236, 238, 324/234; 73/579, 599, 643; 331/157; 318/118

[56] References Cited

U.S. PATENT DOCUMENTS

| 2,401,094 | 5/1946 | Nicholson, Jr. ............... 324/209 X |
| 3,534,254 | 10/1970 | Semienko et al. ............ 324/209 |
| 3,623,358 | 11/1971 | Sugimoto ........................ 73/579 |
| 3,706,026 | 12/1972 | Johnson, Jr. et al. ......... 324/209 |
| 3,786,672 | 1/1974 | Gaerttner ..................... 73/599 X |
| 4,446,427 | 5/1984 | Lourenich .................. 324/236 X |

FOREIGN PATENT DOCUMENTS

1545590 11/1968 France .

OTHER PUBLICATIONS

"Damping Near the Snoek Peak in Fe", E. T. Stephenson and G. P. Conard, Acta *Metallurgica*, vol. 16, Oct. 1968.
"Snoek Peaks and Their Stability in Annealed and Deformed Tantalum", Z. S. Szkopiak and W. Eliasz, *Journal of the Less-Common Metals*, 11 (1966) pp. 273–285.
Beaton, "Apparatus for the Determining of Internal Friction. . ." *Journal of Scientific Instruments (Journal of Physics E)*, Jul. 1968, pp. 735–737.
Eder et al., "A Fast Digital Method for the Measurement of. . ." *Journal of Physics E: Scientific Instruments*, Jun. 1974, pp. 476–480.
van Essen et al., "Measurements of Low Frequency Internal. . ." *Journal of Physics E: Scientific Instruments*, May 1974, pp. 343–345.
Adams et al., "Resonance Testing of Cast Iron" *Journal of Nondestructive Evaluation*, Mar. 1981, pp. 65–74.
Detweiler et al., "Apparatus for the Precision Measurement. . ." *The Review of Scientific Instruments*, Nov. 1968, pp. 1727–1730.

Primary Examiner—Reinhard J. Eisenzopf
Assistant Examiner—Warren S. Edmonds
Attorney, Agent, or Firm—Fay, Sharpe, Beall, Fagan, Minnich & McKee

[57] ABSTRACT

The apparatus includes excitation windings (5, 6, 7) for imparting to an elongate specimen (1) of ferromagnetic material longitudinal oscillations. A device (30) is provided for cutting off a power amplifier (21) of one (5) of the excitation windings, along with a device (28, 29, 30, 32, 33) for detecting and counting the damped oscillations, after the cutting off of the excitation, whose amplitude is greater than or equal to the initial amplitude of the oscillations multiplied by a coefficient so as to permit the determination of the coefficient of internal friction. The excitation winding are constituted by three coaxial cylindrical windings (5, 6, 7) disposed around the specimen (1).

23 Claims, 12 Drawing Sheets

FIG._3

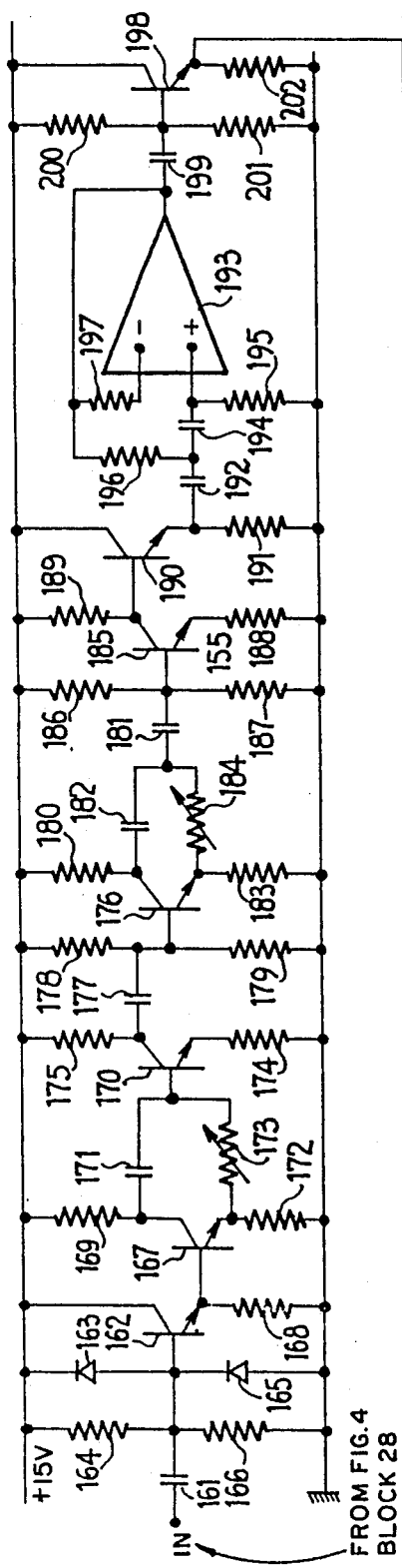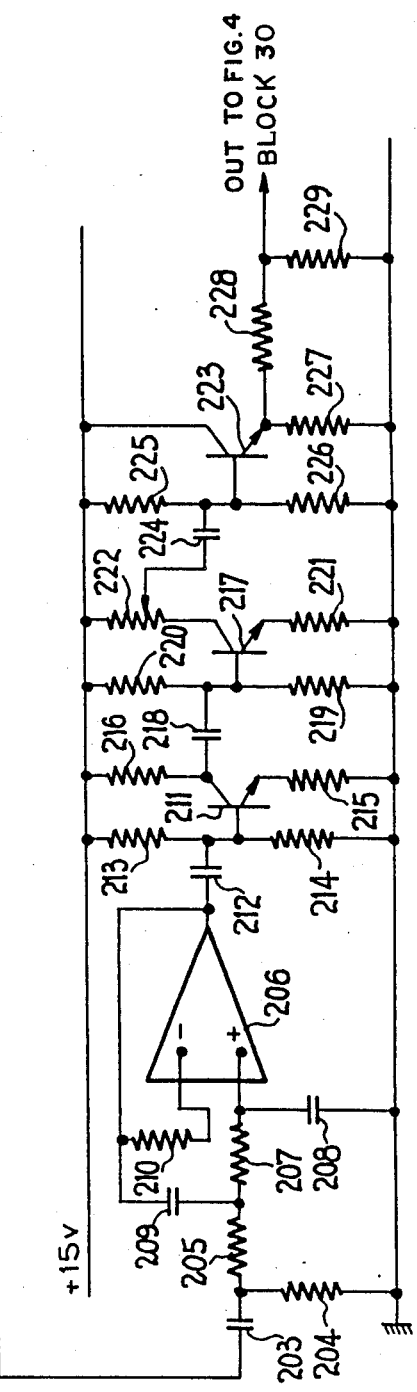
FIG.7

METHOD AND APPARATUS FOR DETERMINING THE COEFFICIENT OF INTERNAL FRICTION OF STEEL OR THE LIKE

The present invention relates to a process and a device for determining the coefficient of internal friction of an elongate specimen of ferromagnetic material, and in particular for determining the content of interstitial elements of the latter wherein the content of interstitial elements may be thought of as atoms located at interstitial sites.

On the macroscopic scale, the internal friction, that property of a solid material that permits of mechanical energy absorption usually as low stress levels of vibration with resultant transfer of the mechanical energy into heat energy is manifested by a delay in the appearance of a deformation of a specimen when a stress is applied to the latter. This delay phenomenon is still termed relaxation. In the case where a sinusoidal stress is applied to the specimen, the deformation of the latter is also sinusoidal and the internal friction is then manifested by a phase shift $\phi$ between the stress and the deformation. The coefficient of internal friction $Q^{-1}$ is then defined by the following relation:

$$Q^{-1} = \tan \phi.$$

In the absence of internal friction, this coefficient $Q^{-1}$ is nil and the deformation is in phase with the stress.

In practice, this coefficient of internal friction $Q^{-1}$ is determined from the measurement of the logarithmic decrement of the vibrations of a freely-oscillating specimen, by the relation:

$$Q^1 = d_{1n}/\pi$$

Note that the logarithmic decrement $d_{1n}$ is the natural logarithm of the ratio of two amplitudes of successive vibrations.

When the temperature of the specimen or its frequency of vibration is varied, the coefficient of internal friction $Q^{-1}$ passes through one or more maxima, termed Snoek peaks, each corresponding to one type of interstitial elements.

The height of this or these peaks is proportional to the content of corresponding interstitial elements in the specimen and it is therefore possible to determine from these measurements the content of interstitial elements of the considered specimen.

On the atomic scale, the internal friction is explained by a movement of the interstitial atoms under the effect of an instantaneous stress, a part of these elements diffuse toward other interstices having a different orientation. The time required for the rearrangement of the interstitial elements is termed the relaxation time.

Under the action of a sinusoidal stress, the interstitial elements jump alternately from one site to the other. This movement enters into resonance at the temperature of the Snoek peak which is the higher as the frequency of vibration is larger. The damping of the oscillations is then maximum.

A certain number of apparatus exist in the prior art for measuring this internal friction due to the interstitial elements in the steel.

In all these known devices, the specimen is made to oscillate under the effect of an excitation. This excitation is then stopped so that the specimen oscillates freely and it is possible to measure the damping of the oscillations.

The mode of deformation and the geometry of the specimen govern the frequency of the oscillations and therefore the temperature range of the test.

There is for example known in the art the Chevenard oscillator or Kê pendulum which is a torsion pendulum comprising an inertia flywheel suspended from the specimen which is in the form of a wire. The Snoek peak is obtained by measuring the damping of the oscillations at different temperatures.

Many improvements have been made in this basic apparatus and have resulted for example in the inverted pendulum, Boulanger's double pendulum and Colette's double pendulum. Among these three mentioned pendulums, Colette's double pendulum has the advantage of permitting measurements to be taken on specimens in the form of a blade.

Systems oscillating under flexion are also known in the art.

However, all these devices have a number of drawbacks.

Indeed, these devices are relatively fastidious to employ. They usually require a relatively large amount of material and a very qualified personnel. Further, these devices give no indication of the kinetics of precipitation of the interstitial elements, except in the case where additional artifical aging treatments are carried out.

An object of the invention is therefore to solve the problems mentioned hereinbefore by proposing a process and a device for determining the coefficient of internal friction which permit effecting measurements on simple specimens, which are very rapidly and very simply employed with a good accuracy of the results. Further, this process and this device also have a high selectivity of the causes of internal friction by minimizing the internal friction produced by phenomena other than those related to interstitial elements.

Another object of the invention is to provide a process and a device which provide complementary items of information concerning the kinetics of precipitation of carbon or nitrogen in the steel and may be integrated within the framework of the control of the manufacture of a larger unit.

The invention therefore provides a process for determining the coefficient of internal friction of an elongate specimen of ferromagnetic material, in particular for determining the content of the interstitial elements of said material, said process comprising electromagnetically exciting the specimen so as to impart longitudinal oscillations propagating the length of the specimen, cutting off the excitation, measuring the attenuation of these oscillations by counting the number N of damped oscillations whose amplitude is greater than or equal to the initial amplitude of said oscillations multiplied by a coefficient $\alpha$, and determining the coefficient of internal friction of the specimen from said number of oscillations.

According to another aspect, the invention also provides a device for determining the coefficient of internal friction of an elongate specimen of ferromagnetic material, in particular for determining the content of interstitial elements of said material, said device comprising excitation means for electromagnetically imparting longitudinal oscillations to said specimen, means for cutting off the excitation means, means for detecting and counting damped oscillations after cutting off said excitation, whose amplitude is greater than or equal to the initial amplitude of the oscillations, multiplied by a coefficient α so as to permit the determination of the coefficient of internal friction.

According to another aspect, the invention also provides an application of the process defined hereinbefore in the study of the kinetics of precipitation of an interstitial element in steel, wherein the temperature of the specimen is maintained constant at a given value corresponding to Snoek's peak for the considered interstitial elements, measuring the variation of the height of the Snoek peak as a function of time, and deducing the kinetics of precipitation from the kinetics of the lowering of the peak.

A better understanding of the invention will be had from the following description, which is given solely by way of example with reference to the accompanying drawings in which:

FIG. 7 is a diagram of the amplifying and filtering means which are part of the construction of a device according to the invention;

The process for determining the coefficient of internal friction according to the invention comprises electromagnetically exciting an elongate specimen of ferromagnetic material so as to impart longitudinal oscillations thereto, cutting off said excitation, measuring the attenuation of said oscillations by counting the number N of damped oscillations whose amplitude is greater than or equal to the initial amplitude multiplied by a coefficient α and determining the coefficient of internal friction from said number of oscillations.

Indeed, the use of longitudinal vibrations permits an increase in the frequency of vibration of the specimen resulting in a reduction in the measuring time and an improvement in the precision of the measurement.

The natural frequency of the vibrations of the specimen may be calculated by means of the following relation:

$$f = \sqrt{\frac{E}{4d\, l^2}}$$

in which E designates the modulus of elasticity of the material, l the length of the specimen, d the density of the material and f the fundamental frequency of the longitudinal vibrations of the specimen in resonance.

Thus, for example, in the case of a mild steel specimen having a length of 100 mm, the natural frequency of the vibrations is around 25 KHz.

The specimen is maintained in oscillation by magnetostriction, as will be described hereinafter.

Figure 1:
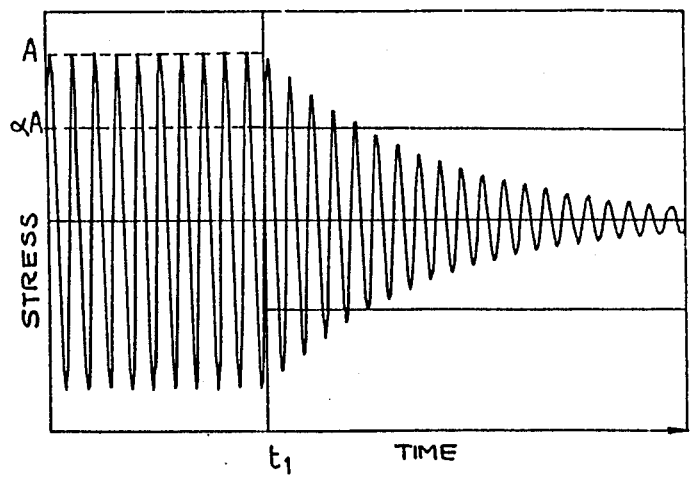
FIG. 1 is a graph illustrating the evolution of a stress in the course of a measurement of the coefficient of internal friction.

As shown in FIG. 1, a specimen is subjected to sustained oscillations up to time t1 corresponding to the cutting off of the excitation thereof. After t1, and therefore after the cutting off of the excitation, the specimen is in the condition of damped oscillations which permits the determination of the coefficient of internal friction of this specimen, by counting the number N of damped oscillations, whose amplitude is greater than or equal to the initial amplitude A of these oscillations multiplied by a coefficient α.

Thus, in the example shown in FIG. 1, this number N is equal to 5. With this number of damped oscillations, the coefficient $Q^{-1}$ of friction is determined from the following relation:

$$Q^{-1} = (L_n(1)/\alpha)/\pi N$$

In the case of this FIG. 1, the coefficient α is equal to 0.54, which permits the determination of the coefficient of internal friction $Q^{-1}$ of the specimen tested by the aforementioned relation and the obtainment of $Q^{-1} = 392 \times 10^{-4}$.

Note that, during this measurement, this specimen is brought to the temperature of the Snoek peak which, under these operating conditions, is about 185° C. for carbon and 165° C. for nitrogen.

Thus the temperature of the specimen may be fixed for the Snoek peak and the isothermal evolution of the coefficient of internal friction $Q^{-1}$ may be observed with respect to time, so that there are obtained with good accuracy the height of the initial Snoek peak and the kinetics of the lowering of the peak, i.e. the kinetics of precipitation of the considered interstitial element An application of the process just described therefore consists in the study of the kinetics of precipitation of an interstitial element in steel, in which the temperature of the specimen is maintained constant at a given value corresponding to the Snoek peak for the considered interstitial element, the variation of the height of the Snoek peak as a function of time is measured and the kinetics of precipitation is deduced from the kinetics of the lowering of the peak.

However, it is also possible to vary the temperature of the specimen so as to make appear the Snoek peak representing the coefficient of internal friction $Q^{-1}$ as a function of the temperature, the height of this peak being a linear function of the concentration of interstitial elements of the material, for example of carbon or nitrogen. However, it is difficult to scan sufficiently, rapidly a temperature range of the specimens to avoid a precipitation by an artificial aging.

Figure 2:
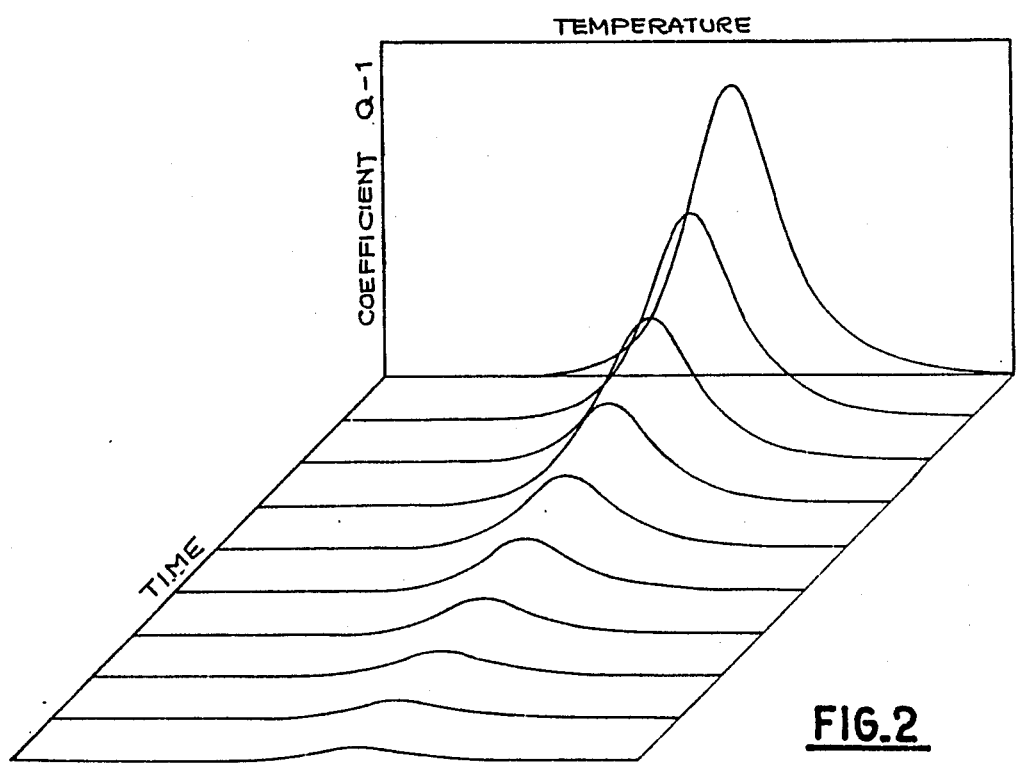
FIG. 2 is a graph illustrating the evolution of the coefficient of internal friction with respect to time and temperature.

An example of the variation of the coefficient of internal friction $Q^{-1}$ with respect to time, corresponding to the kinetics of precipitation, and with respect to temperature, corresponding to the Snoek peak, is represented in FIG. 2.

Figure 3:
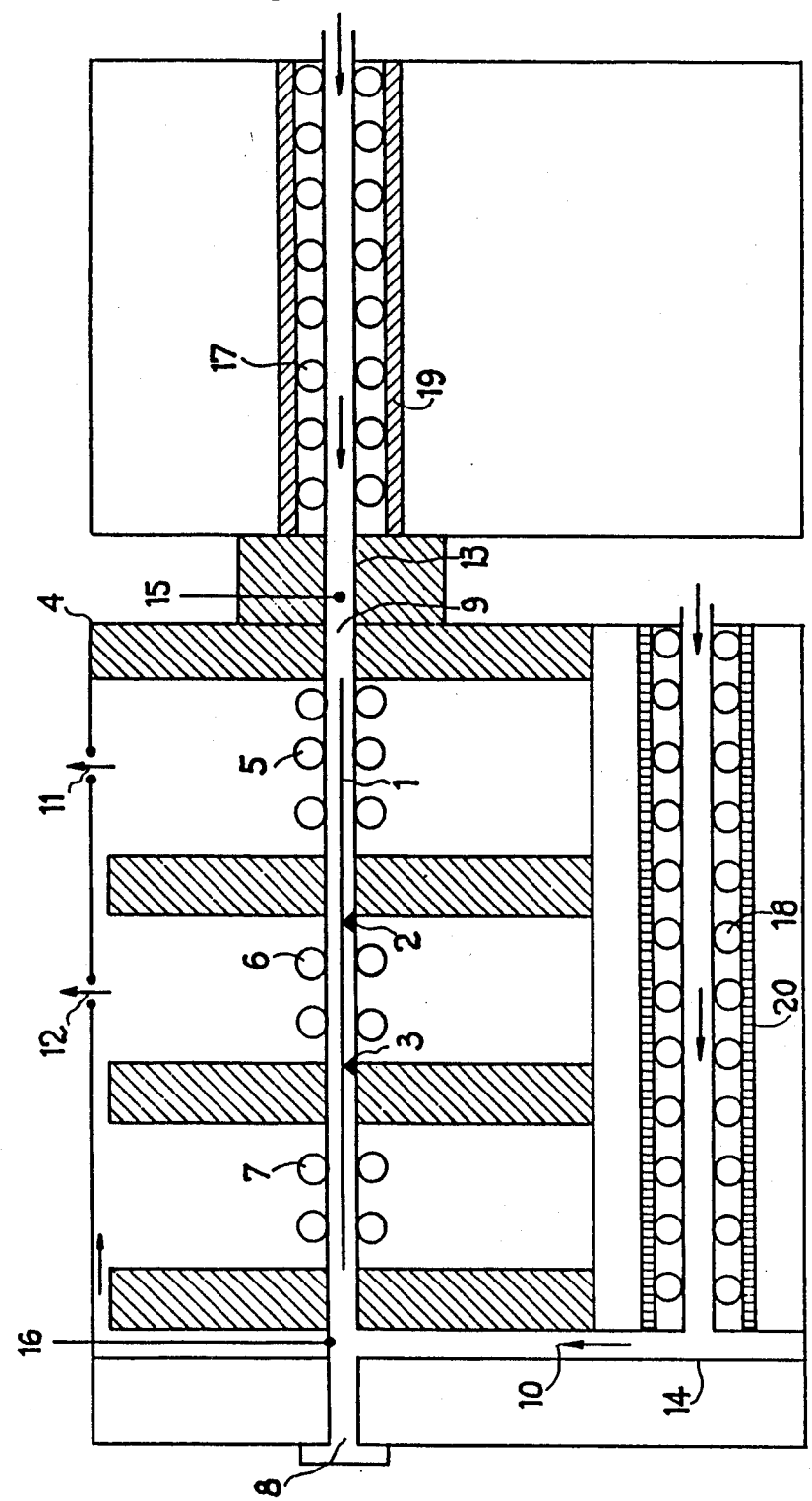
FIG. 3 is a view of a measuring enclosure which is part of a device according to the invention.

The measurements are carried out in cell diagrammatically shown in FIG. 3. An elongate specimen 1 of ferromagnetic material rests on support members 2 and 3 of insulating material, for example constituted by blades of Teflon and disposed inside a heated measuring cell or enclosure 4.

Disposed inside this heated cell 4 are three coaxial cylindrical windings surrounding the specimen 1. These three windings comprise a primary winding 5 disposed around one of the end portions of the specimen and connected, as will be explained hereinafter, to a first supply source for oscillating the specimen 1 by magnetostriction in the longitudinal direction. A polarization winding 6 is disposed around the central portion of the specimen and connected to second supply means for ensuring a magnetic polarization of the specimen. A secondary winding 7 is disposed around the other end portion of the specimen and connected to means for detecting and counting the damped oscillations.

The cell comprises a first opening 8 for the passage of the specimen into the cell and air inlets 9 and 10, connected to hot-air blowing means, constituting heating means for the cell. Openings 11 and 12 are also provided in the walls of the cell 4 for the outlet of air.

The two hot-air inlets 9 and 10 of the cell are connected to heating means through conduits 13 and 14, the conduit 13 opening out in facing relation to the specimen so as to heat directly the latter by convection. Means for controlling the temperature, for example constituted by thermocouples of Chromel/Alumel 15 and 16 disposed in the hot-air blowing conduits, enable the temperature of the air blown into the enclosure to be controlled so as to regulate the latter in a relatively precise manner.

The air heating means are constituted by heating resistors 17 and 18 disposed around air inlet conduits so as to heat the air circulating in these conduits which are themselves surrounded by insulating tubes 19 and 20.

Figure 4:
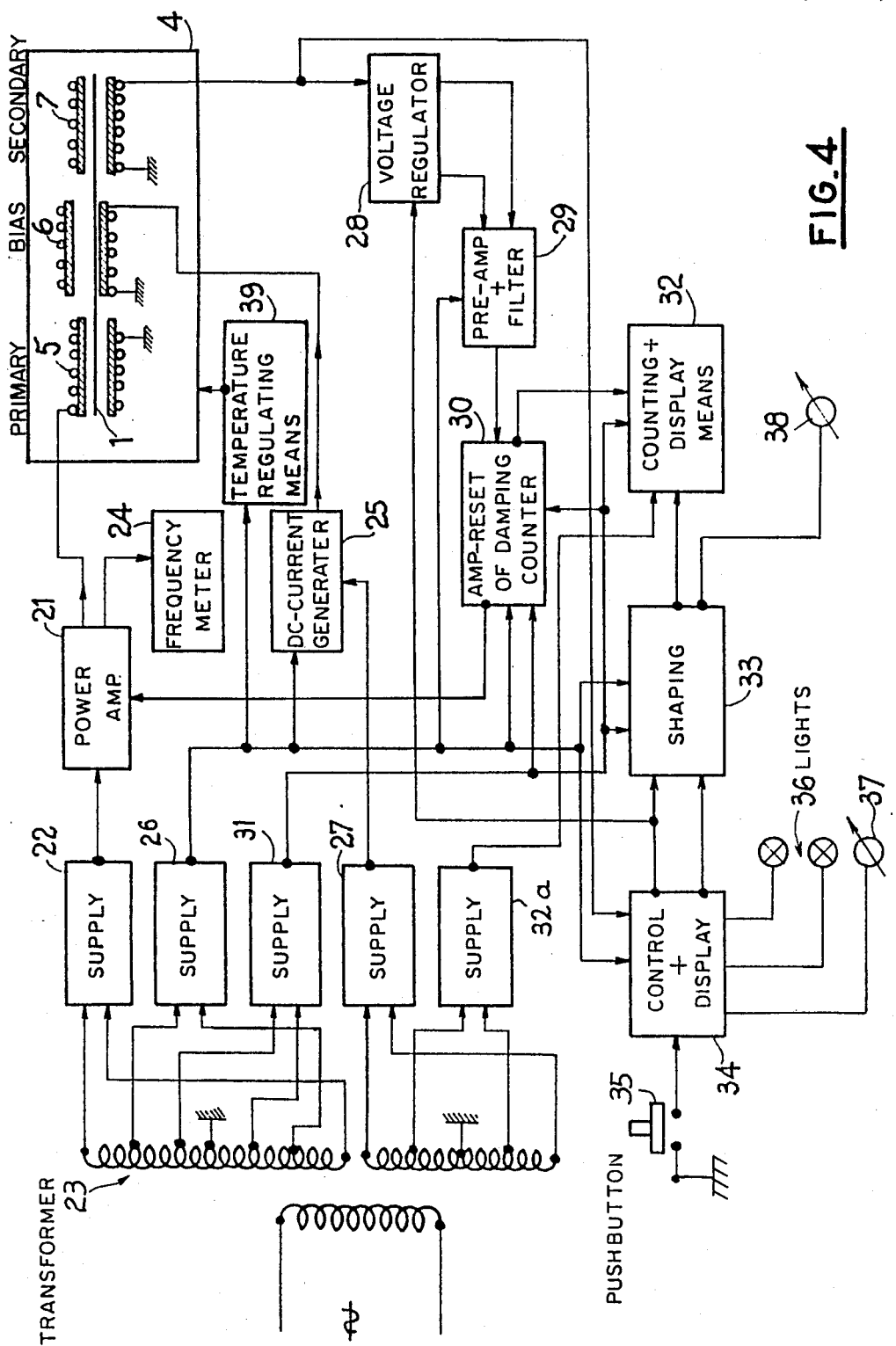
FIG. 4 is a block diagram of the various elements in the construction of a device according to the invention.

As can be seen in FIG. 4, the primary winding 5 is connected to the output of a power amplifier 21 whose input is connected to supply means 22 which are connected to an output of a transformer 23 connected to the main supply. A frequencymeter 24 is also connected to the output of the power amplifier 21 so as to ascertain the frequency of the oscillations imparted to the specimen 1.

The polarization winding 6 is connected to the output of a current generator 25 whose two inputs are connected to supply means 26 and 27. The inputs of these supply means are connected to the outputs of the transformer 23.

The secondary winding 7 is connected to the input of the voltage regulation means 28 whose outputs are connected to the inputs of pre-amplifying and filtering means 29. The output of these pre-amplifying and filtering means 29 is connected to the input of means 30 for amplifying and resetting a damping counter whose output is connected to the power amplifier 21 supplying the primary winding. These means 30 are also connected to the supply means 26 and to supply means 31. An output of the means 30 is connected to counting and display means 32 having an input connected to supply means 32a and another input connected to shaping means 33. The input of these shaping means 33 is connected to control and display means 34 whose input is controlled by a damping test pushbutton 35.

A number of lights 36 show the state of the device by indicating the operating mode of the device. A slider sometimes referred to as an adjustable switch 37 is also disposed on the control means 34 to permit the regulating of the amplitude of the voltage coming from the secondary winding.

Another slider 38 is also connected to the shaping means 33 for regulating the amplitude of the counting voltage.

The apparatus becomes operational when power is supplied to supplies 22, 26, 31, 27 via the transformer 23. The temperature inside cell 4 is increased to a predetermined setting thereby raising the specimen to the desired temperature.

A direct current therefore passes through the polarization winding so as to subject the specimen to a uniform magnetic field which increases its permeability. The coefficient of coupling between the primary and secondary windings therefore increases and this initiates oscillations in the specimen at the natural frequency of each specimen, under the effect of the excitation of the latter by the primary winding 5, which is consequently supplied in such manner as to vibrate the specimen by the magnetostriction effect. The excitation of the specimen and its magnetic polarization then produce an induced electromotive force, which is a function of the specimen, in the secondary winding. Specifically, the primary winding (5) is supplied with a signal from the power amplifier (21) which is driven with a signal provided from the natural frequency created at the secondary winding (7), after such signal has been regulated (28), filtered (29), and amplified (30). Note that this induced voltage comes from a variation of the magnetic flux and the latter comes from a variation of the permeability (Vilari effect) and not from a variation of length. Indeed, the deformation of the specimen remains less than $10^{-4}\%$ and may therefore be ignored. The temperature inside the cell is brought to, for example, $185°\pm1°$ C. by blowing means as explained in conjunction with FIG. 3 and this temperature is maintained constant by temperature regulating means 39.

Figure 9:
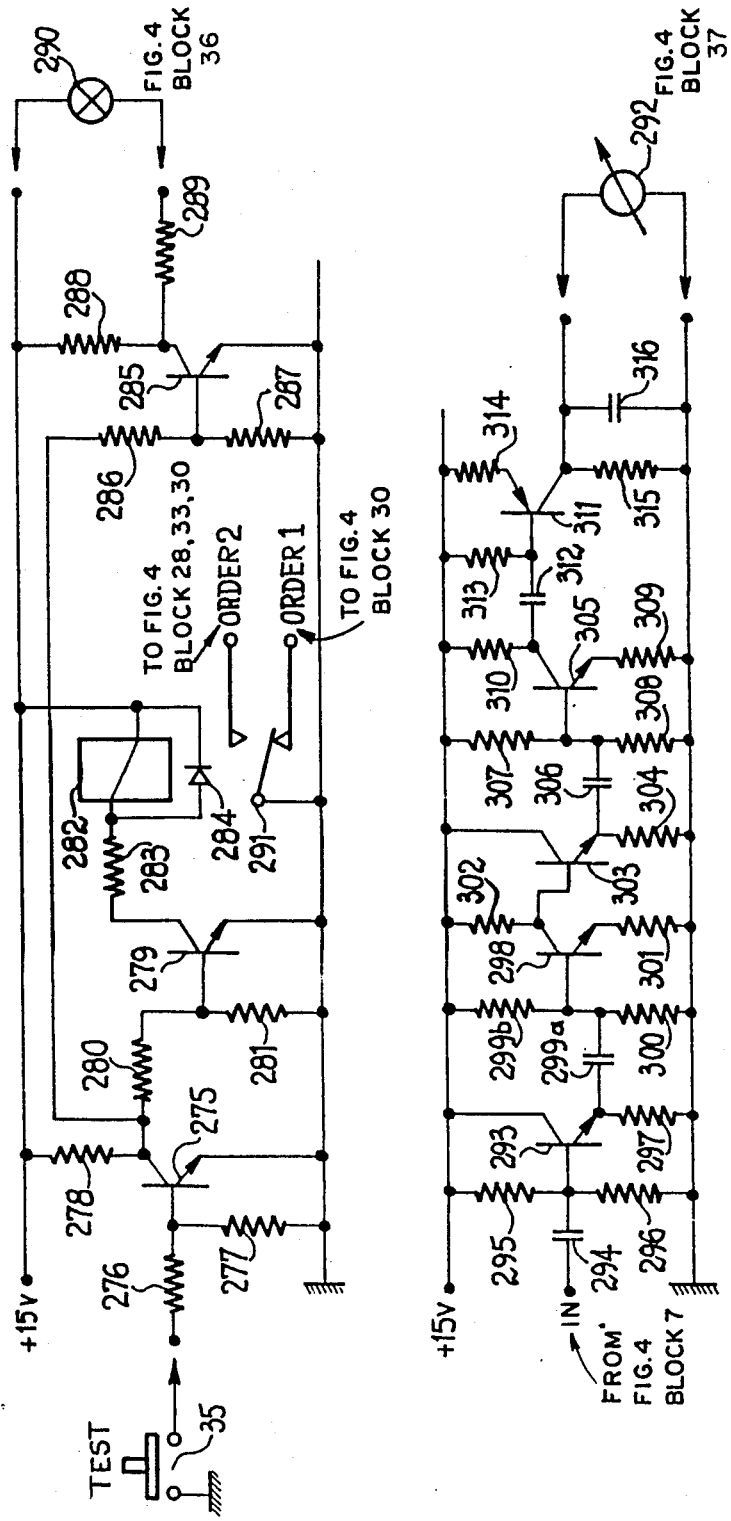
FIG. 9 is a diagram of a control circuit which is part of the construction of a device according to the invention.

When the specimen is oscillating at a high enough frequency the damping test pushbutton 35, is actuated causing the supply of the primary winding to be cut off by the stopping of the power amplifier 21. This is accomplished by altering the signal on the Order 2 signal line being sent from the control 34 to the logic circuitry of the means for amplifying and resetting 30. The aforementioned description may be clarified by referring to FIG. 9. The specimen is then subjected to damped oscillations. The output of these oscillations are picked off at the output of the secondary winding 7 sent to the control means 34 and the shaping means 33 so that the counting means 32 can count the number of oscillations whose amplitude is greater than the initial amplitude of the oscillations multiplied by a coefficient $\alpha$ equal, for example, to 0.54, and display the result and permit the calculation of the coefficient of internal friction by means of the aforementioned relation.

Figure 5:
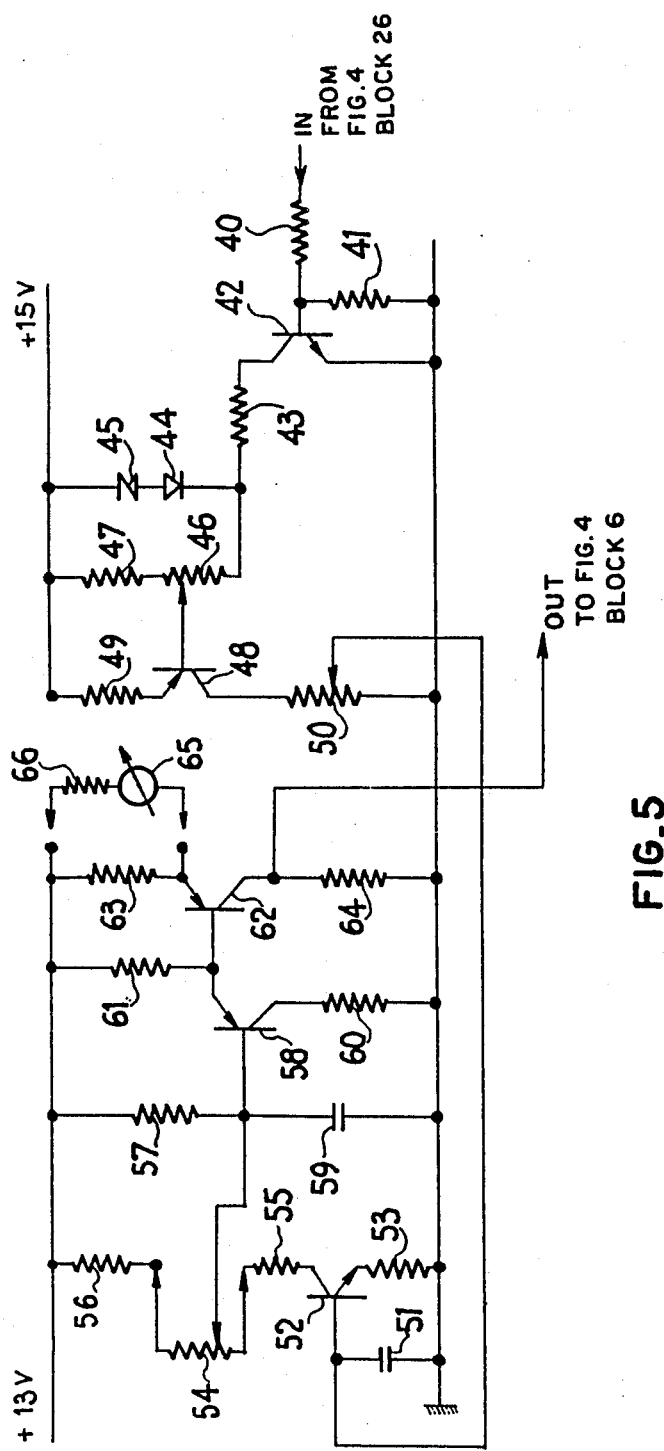
FIG. 5 is a diagram of a current generator which is part of the construction of a device according to the invention.

The polarization winding 6 therefore receives a direct current from the current generator 25 which is for example constituted by the circuit represented in FIG. 5. The initiating signal, which may be automatic or manual, is applied to a terminal IN of a resistor 40 whose other terminal is connected to ground through a resistor 41 and to the base of an NPN transistor 42. The emitter of the transistor 42 is connected to the ground and its collector is connected to a terminal of a resistor 43 whose other terminal is connected to a +15 V supply terminal through a diode 44 and a Zener diode 45 which are inverse-connected. A potentiometer 46 and a resistor 47 in series are connected in parallel to the terminals of these diodes 44 and 45. The slider of the potentiometer 46 is connected to the base of a PNP transistor 48 whose emitter is connected to the +15 V supply through a resistor 49. The collector of this transistor 48 is connected to the ground through a potentiometer 50. The slider of this potentiometer is connected to the ground through a capacitor 51 and to the base of an NPN transistor 52. The emitter of this transistor 52 is connected to the ground through a resistor 53 and its collector is connected to a terminal of a potentiometer 54 through a resistor 55. The other terminal of this potentiometer 54 is connected to a +13 V supply terminal through a resistor 56. The slider of this potentiometer 54 is connected to the +13 V supply through a resistor 57, to the base of a PNP transistor 58 and to the ground through a capacitor 59. This collector of this PNP transistor 58 is connected to the ground through a resistor 60. The emitter of this transistor is connected to the +13 V supply through a resistor 61. This emitter is also connected to the base of a PNP transistor 62 whose emitter is connected to the +13 V supply through a resistor 63 and whose collector is connected to the ground through a resistor 64.

An off-on control device 65 in series with a resistor 66 is connected in parallel to the terminals of the resistor 63. The collector of the transistor 62 is connected to one of the terminals of the polarization winding 6 so as to supply thereto a current for the magnetic polarization of the specimen. The transistors 52 and 58 constitute a first current generator which fixes the voltage on the base of the transistors 58 and 62 which fixes the current sent to the polarization winding 6.

The authorization for the applicatin of this current to the polarization winding 6 is controlled by the application of a voltage, for example of +5 V, on the base of the transistor 42 through the aforementioned initiating signal input. As already explained, this input may be manual or automatic.

The potentiometer 54 may be disposed on the front side of a control panel and enables the polarization current to be varied, for example, from 0 to 3 amps. Moreover, an ammeter disposed on the front side of the control panel also permits a reading of this value of the current.

When this polarization current is applied to the winding 6, and the primary winding 5 is also supplied, there appears at the terminals of the secondary winding 7 an induced sinusoidal voltage which is a function of the specimen 1 disposed in the centre of these windings. The frequency of this signal is, for example, between 24.5 and 26.5 KHz and its amplitude between 0.1 and 1.2 V for the previously-described specimen. The signal received at this secondary winding is applied to the voltage regulating means 28. These regulating means are represented in detail in FIG. 6. The output signal of the secondary winding is applied to a terminal IN of a capacitor 70 whose other terminal is connected to the +15 V supply through a resistor 71 and to a reference line A through a resistor 72. This terminal of the capacitor 70 is also connected to the base of an NPN transistor 73 whose collector is connected to the +15 V and whose emitter is connected to the reference line A through a potentiometer 74. The slider of this potentiometer is connected to the base of an NPN transistor 75 through a capacitor 76 and this base of the transistor 75 is connected to the +15 V through a resistor 77 and to the line A through a resistor 78. The collector of this transistor 75N is connected to the +15 V and its emitter is connected to the line A through a resistor 79.

The emitter of this transistor 75 is also connected to the drain of a field-effect transistor 80 through a resistor 81. The grid of this transistor 80 is connected to the line A through a capacitor 82. The drain of this transistor 80 is also connected to the base of an NPN transistor 83 through a capacitor 84. The collector of the transistor 83 is directly connected to the +15 V. The base of the transistor 83 is also connected to the +15 V through a resistor 85 and to the line A through a resistor 86. The source of the transistor 890 is connected to the line A. The emitter of the transistor 83 is connected to the line A through a resistor 87 and to the drain of a field-effect transistor 88 through a resistor 89. The grid of this transistor 88 is connected to the line A through a capacitor 90 and its source is directly connected to the line A. The drain of this transistor 88 is also connected to the base of an NPN transistor 81 through a capacitor 92. This base of the transistor 91 is also connected to the +15 V through a resistor 93 and to the line A through a resistor 94. The emitter of the transistor 91 is connected to the line A through a resistor 95 and its collector is connected to the +15 through a resistor 96 and to the base of an NPN transistor 97 through a capacitor 98. The base of this transistor 97 is connected to the +15 V through a resistor 99 and to the line A through a resistor 100. The emitter of this transistor 97 is connected to the line A through a resistor 101. The collector of this transistor 97 is connected to the +15 V through a resistor 102 and to the base of an NPN transistor 103 whose collector is directly connected to the +15 V. The emitter of this transistor 103 is connected to the line A through a potentiometer 104 whose slider constitutes the output OUT of the regulating means 28. The emitter of the transistor 103 is also connected to the base of a PNP transistor 105 through a capacitor 106 in series with a resistor 107. This base is also connected to the +15 V through a resistor 108 and to the line A through a resistor 109 connected in parallel with a capacitor 110. The collector of this transistor 105 is directly connected to the line A. Its emitter is connected to the +15 V through a resistor 111.

This emitter is also connected to the base of a PNP transistor 112 through a capacitor 113. The base of this transistor is connected to the +15 V through a resistor 114. The emitter of this transistor 113 is connected to the +15 V through a resistor 115 and its collector is connected to the line A through a resistor 116 connected in parallel with a capacitor 117.

This collector is also connected to the inverting input of an operational amplifier 118 through a resistor 119. The output of this operational amplifier 118 is loop-connected to its inverting input through a resistor 120. This inverting input is also connected to a terminal of a resistor 121 whose other terminal is connected to the slider of a potentiometer 122 connected between the ground and the collector of an NPN transistor 123. The non-inverting input of the operational amplifier 118 is connected to the ground through a resistor 124.

The emitter of the transistor 123 is connected to a −15 V supply source through an adjustable resistor 125 connected in series with a resistor 126. The base of this transistor 123 is connected to the −15 V through a Zener diode 127 connected in series with a diode 128, these diodes being connected inversely. This base is also connected to the ground through a resistor 129. The collector of the transistor 123 is also connected to the ground through a potentiometer 130 whose slider is connected through a resistor 131 to the inverting input of an operational amplifier 132. This input is also connected to the output of the operational amplifier 118 through a resistor 133. The non-inverting input of the operational amplifier 132 is connected to the ground through a resistor 134. The output of this operational amplifier 132 is loop-connected to its inverting input through an adjustable resistor 135. The output of this operational amplifier 132 is also connected to the collector of an NPN transistor 136 through a resistor 137. The emitter of this transistor 136 is directly connected to the ground. The collector of this transistor is also connected through a resistor 138 in series with a diode 139, to the grid of the aforementioned field-effect transistor 88. This grid is also connected to the +15 V through a diode 140, a resistor 141 and a resistor 142 connected in series. The collector of the transistor 136 is also connected, through a resistor 143 and a diode 144, to the grid of the field-effect transistor 80. This grid is also connected through a diode 145 and a resistor 146 to the collector of an NPN transistor 147 to which is connected the resistor 142 connected to the aforementioned +15 V. The emitter of this transistor 147 is connected to the reference line A. The base of this resistor is also connected to this reference line A through a resistor 148 and through a resistor 149 to an input of a NAND gate 150 and to the output of a NAND gate 151. The base of the NPN transistor 136 is connected to the ground through a resistor 152, to the input of the NAND gate 151 and to the output of the NAND gate 150 through a resistor 153. One of the inputs of the NAND gate 150 is connected to the output of a NAND gate 154 whose inputs are connected to the collector of an NPN transistor 155 connected to the supply line +15 V through a resistor 156 and to one of the inputs of the NAND gate 151. The emitter of this transistor 155 is directly connected to the ground. The base of this transistor is connected to the ground through a resistor 156 and to a terminal of a resistor 157 whose other terminal is connected to a resistor 158 connected to the supply line +5 V, to a capacitor 159 connected to the ground and to a resistor 160 receiving an ORDER 2 signal which will be described in more detail hereinafter.

The circuit just described therefore constitutes the means for regulating the output signal coming from the secondary winding 7. This signal is regulated by the transistors 80 and 88 which are cascade connected. A reference signal is delivered by the current generator constituted by the transistor 123 and the associated elements, the operational amplifiers 118 and 132 amplifying the error voltage between this reference signal and the output signal of the secondary winding 7 and applying on the grids of the transistors 80 and 88 the result of this amplification.

This output signal of the regulating means is then applied to the pre-amplifying and filtering means 29 which may be constituted, for example, by a circuit as shown in FIG. 7. The output signal of the voltage regulating means 28 is applied to a terminal of a capacitor 161 whose other terminal is connected to the base of an NPN transistor 162 whose collector is connected to the supply line +15 V. This base is also connected to the +15 V through a Diode 163 and a resistor 164 which are connected in parallel. This base is also connected to the ground through a diode 165 and a resistor 166 connected in parallel. The emitter of the transistor 162 is connected to the base of an NPN transistor 167 and to the ground through a resistor 168. The collector of the transistor 167 is connected to the +15 V supply line through a resistor 169 and to the base of an NPN transistor 170 through a capacitor 171. The emitter of the transistor 167 is connected to the ground through a resistor 172 and to the base of the transistor 170 through an adjustable resistor 173. The emitter of the transistor 170 is connected to the ground through a resistor 174. Its collector is connected to the +15 V through a resistor 175 and to the base of an NPN transistor 176 through a capacitor 177. This base is also connected to the +15 V through a resistor 178 and to the ground through a resistor 179. The collector of the transistor 176 is connected to the +15 V through a resistor 180 and to a terminal of a capacitor 181 through a capacitor 182. The emitter of the transistor 176 is connected to the ground through a resistor 183 and to the terminal of the capacitor 181 through an adjustable resistor 184. The other terminal of the capacitor 181 is connected to the base of an NPN transistor 185 which is also connected to the +15 V through a resistor 186 and to the ground through a resistor 187. The emitter of this transistor 185 is connected to the ground through a resistor 188. Its collector is connected on one hand to the +15 V through a resistor 189 and, on the other hand, to the base of an NPN transistor 190 whose collector is directly connected to the +15 V. The emitter of this transistor 190 is connected to the ground through a resistor 191 and to the terminal of a capacitor 192.

The other terminal of this capacitor 192 is connected to the non-inverting input of an operational amplifier 193 through a capacitor 194 and this non-inverting input of the operational amplifier is also connected to the ground through a resistor 195. The common terminal of the capacitors 192 and 194 is also connected to the output of the operational amplifier 193 through a resistor 196. The output of this operational amplifier 193 is loop-connected to its inverting input through a resistor 197. This output of the operational amplifier 193 is also connected to the base of an NPN transistor 198 through a capacitor 199. This base is also connected to the +15 V through a resistor 200 and to the ground through a resistor 201. The collector of the transistor 198 is directly connected to the +15 V. Its emitter is connected to ground through a resistor 202. This emitter is also connected to a terminal of a capacitor 203 whose other terminal is connected, on one hand, to the ground through a resistor 204 and, on the other hand, to a terminal of a resistor 205. The other terminal of this resistor 205 is connected to the non-inverting input of an operational amplifier 206 through a resistor 207, this non-inverting input of the operational amplifier 206 being connected to the ground through a capacitor 208. The common terminal of the resistors 205 and 207 is also connected to the output of the operational amplifier 206 through a capacitor 209. This output of the operational amplifier 206 is also loop-connected to its inverting input through a resistor 210. The output of the operational amplifier 206 is connected to the base of an NPN transistor 211 through a capacitor 212. This base is also connected to the +15 V through a resistor 213 and to the ground through a resistor 214. The emitter of the transistor 211 is connected to the ground through a resistor 215. Its collector is connected to the +15 V through a resistor 216 and to the base of an NPN transistor 217 through a capacitor 218. This base of the transistor 217 is also connected to the ground through a resistor 219 and to the +15 V through a resistor 220. The emitter of the transistor 217 is connected to the ground through a resistor 221 and its collector is connected to the +15 V through a potentiometer 222 whose slider is connected to the base of an NPN transistor 223 through a capacitor 224. The base of this transistor 223 is also connected to the +15 V through a resistor 225 and to the ground through a resistor 226. The collector of this transistor 223 is directly connected to the +15 V. The emitter of this transistor is connected to the ground through a resistor 227 and to a terminal of a resistor 228 whose other terminal is connected to the ground through a resistor 229 and constitutes the output of the aforementioned pre-amplifying and filtering means.

The output signal of the secondary winding after passage through the voltage regulating means is then filtered, put into phase and amplified. This filtering is achieved by a low-pass filter constituted by the operational amplifier 193 and the associated elements and by a high-pass filter constituted by the operational amplifier 206 and the associated elements. The signal is put into phase by two RC circuits connected around the transistors 167 and 176. The amplification of the signal is effected by the transistors 211, 217 and 223 providing an output signal which is sufficient to correctly drive the power amplifier 21 through the aforementioned means 30.

Figure 8:
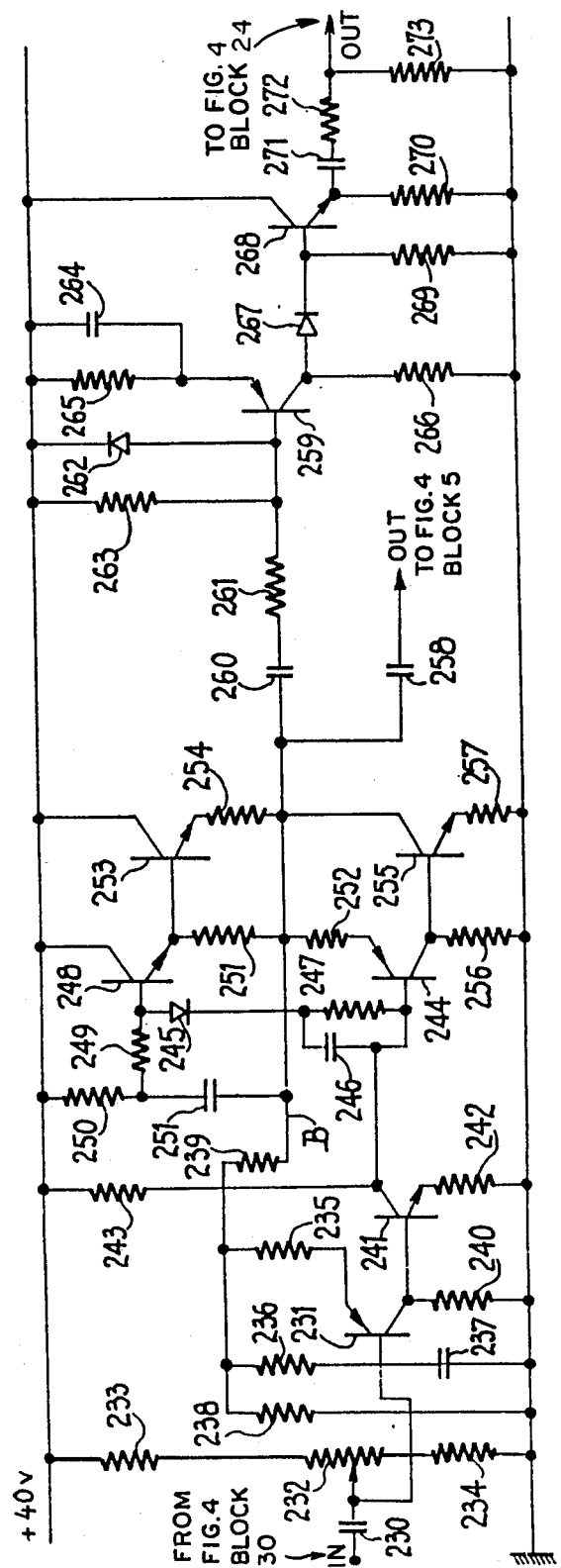
FIG. 8 is a diagram of a power amplifier which is part of the construction of a device according to the invention.

This power-amplifier 21 is, for example, constituted by a circuit such as that shown in FIG. 8. The output of the pre-amplifying and filtering means is applied to a terminal of a capacitor 230 whose other terminal is connected to the base of a PNP transistor 231 and to the slider of the potentiometer 232 connected, on one hand, to a +40 V supply source through a resistor 233 and, on the other hand, to the ground through a resistor 234. The emitter of the transistor 231 is connected to a terminal of a resistor 235 whose other terminal is connected to the ground through a resistor 236 which is connected in series with a capacitor 237 and a resistor 238 which is connected in parallel to this resistor and this capacitor. This transistor 235 is also connected to a terminal of a resistor 239 whose other terminal delivers a reference level B.

The collector of the transistor 231 is connected to the ground through a resistor 240 and to the base of an NPN transistor 241 whose emitter is connected to the ground through a resistor 242. The collector of this transistor 241 is connected to the +15 V through a resistor 243 and to the base of PNP transistor 244. This base is also connected to the cathode of a diode 245 through a capacitor 246 connected in parallel with a resistor 247. The anode of this diode 245 is connected to the base of an NPN transistor 248 whose collector is directly connected to the +40 V. This base is also connected to a terminal of a resistor 249 whose other terminal is connected, on one hand, to the +40 V through a resistor 250 and, on the other hand, to the reference line B through a capacitor 251. The emitter of the transistor 248 is connected to the reference line B through a resistor 251 and the emitter of the transistor 244 is connected to this line B through a resistor 252. The emitter of the transistor 248 is also connected to the base of an NPN transistor 253 whose collector is connected to the +40 V. The emitter of this transistor is connected through a resistor 244 to the line B. The latter is also connected to the collector of an NPN transistor 255 whose base is connected to the collector of the transistor 244. The base of this transistor 245 is also connected to the ground through a resistor 256. The emitter of this transistor is connected to the ground through a resistor 257.

This reference line B is also connected to a terminal of a capacitor 258 whose other terminal constitutes the output of the power amplifier adapted to supply power to the primary winding. This reference line B is also connected to the base of a PNP transistor 259 through a capacitor 260 and a resistor 261 connected in series. The base of this transistor 259 is also connected to the +40 V through a diode 262 and a resistor 263 connected in parallel. The emitter of this transistor 259 is connected to the +40 V through a capacitor 264 connected in parallel with a resistor 265. The collector of the transistor 259 is connected to the ground through a resistor 266 and to the base of a transistor 268 through a diode 267. This base of the transistor 268 is also connected to the ground through a resistor 269. The collector of this transistor is directly connected to the +40V and its emitter is connected to the ground through a resistor 270. This emitter is also connected to a terminal of a capacitor 271 whose other terminal is connected to a terminal of a resistor 272 whose other terminal is connected to the ground through a resistor 273 and constitutes the output of the power amplifier delivering the signal intended for the aforementioned frequencymeter 24.

This example of amplifier just described operates in class AB. The circuit constituted by the transistors 259 and 268 constitutes means for shaping the signal of the power amplifier so as to be able to apply it to the frequency meter.

Note that, in a modification of the device, the voltage induced in the secondary winding 7 may be maintained constant by action on the rate of amplification of the signal sent to the primary winding by this amplifier, for the purpose of minimizing and controlling at a constant level the dissipation of energy by the Vilari effect which is proportional to the magnetic flux and therefore to the induced voltage.

Figure 6:
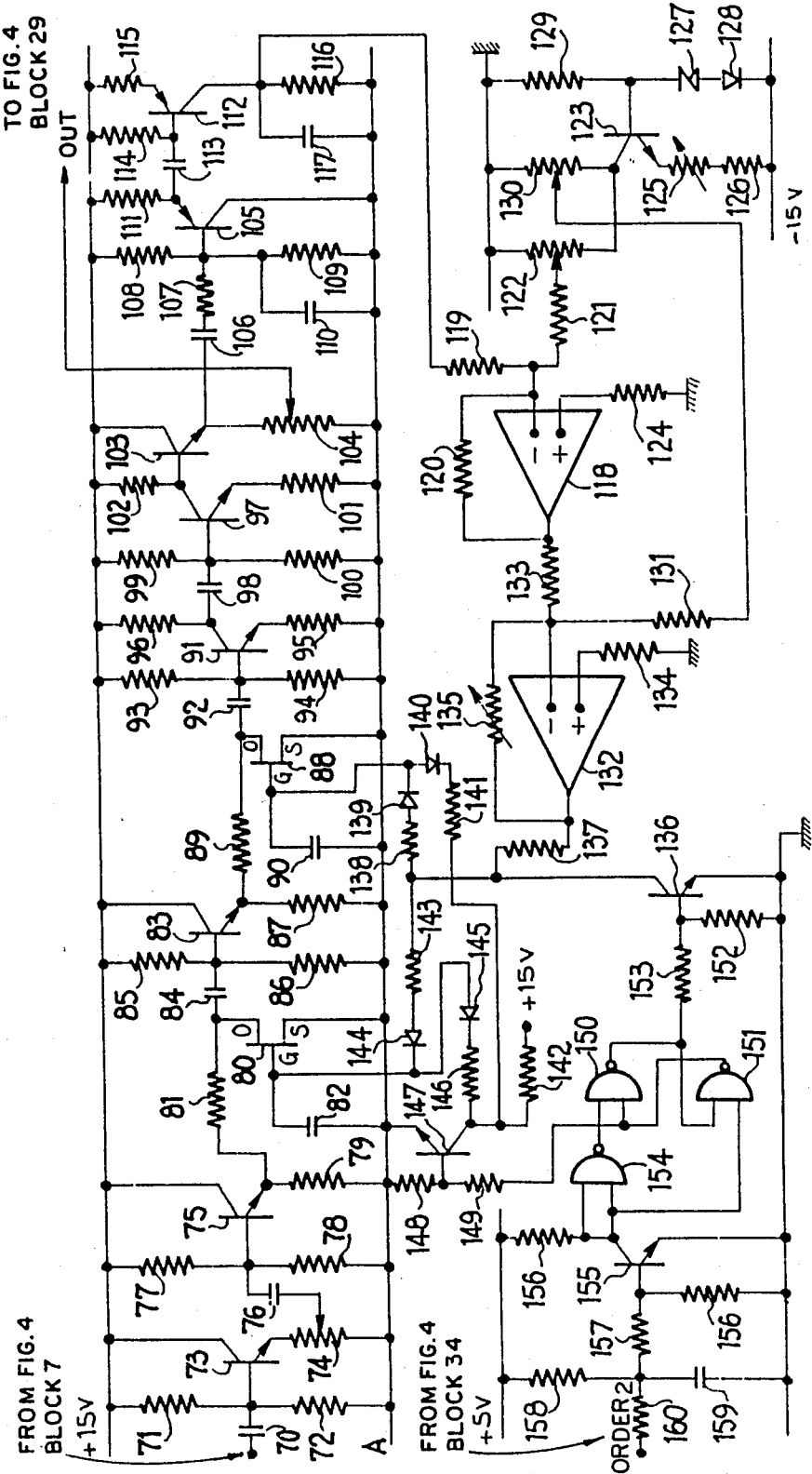
FIG. 6 is a diagram of a voltage regulator which is part of the construction of a device according to the invention.

The control of the various elements just described is effected by the aforementioned control and display means. These means are constituted for example by a circuit such as that shown in FIG. 9. There is seen in this FIG. 9 the test push-button 35 one of the terminals of which is connected to the ground whereas the other terminal is connected to the base of an NPN transistor 275 through a resistor 276. This base of the transistor 275 is also connected to the ground through a resistor 277. The emitter of this transistor is directly connected to the ground. The collector of this transistor is connected to the +15 V supply voltage through a resistor 278. This collector is also connected to the base of an NPN transistor 27c through a resistor 280. This base is also connected to the ground through a resistor 281. The emitter of the transistor 279 is directly connected to the ground. The collector of this transistor 279 is connected to a relay 282 through a resistor 283. A protection diode 294 is connected to the terminals of this relay which is also connected to the +15 V supply. The collector of the transistor 275 is also connected to the base of an NPN transistor 295 through a resistor 286 and this base is also connected to the ground through a resistor 287. The emitter of this transistor 285 is connected to the ground and its collector is connected to the +15 V through a resistor 288. This collector is also connected to a terminal of a resistor 289 whose other terminal constitutes, with the +15 V terminal of the supply, supply terminals for example of a light 290 indicating to a user that the device is operating in its test mode. The relay 282 controls a contact 291 having two positions which, in one of its positions, delivers an ORDER 1 signal whose function will be explained in more detail hereinafter and in the other position, an ORDER 2 signal which, as explained before, is applied to the voltage regulating means through the resistor 160, as shown in FIG. 6.

These control and display means further comprise a second circuit for applying to a voltmeter 292 a signal indicating the amplitude of the voltage at the terminals of the secondary winding.

The signal coming from the secondary winding is applied to the base of an NPN transistor 293 through a capacitor 294. The base of this transistor 293 is connected to the +15 V supply through a resistor 295 and to the ground through a resistor 296. The collector of this transistor 293 is connected to the +15 V. The emitter of this transistor is connected to the ground through a resistor 297 and to the base of an NPN transistor 298 through a capacitor 299a. This base of the transistor 298 is connected to the +15 V through a resistor 299b and to the ground through a resistor 300. The emitter of the transistor 298 is connected to the ground through a resistor 301. Its collector is connected, on one hand, to the +15 V through a resistor 302 and, on, the other hand, to the base of an NPN transistor 303 whose collector is connected to the +15 V. The emitter of this transistor 303 is connected to the ground through a resistor 304 and to the base of an NPN transistor 305 through a capacitor 306. The base of this transistor 305 is connected to the +15 V through a resistor 307 and to the ground through a resistor 308. The emitter of the transistor 305 is connected to the ground through a resistor 309 and its collector is connected to the +15 V through a resistor 310. The collector of the transistor 305 is also connected to the base of a PNP transistor 311 through a capacitor 312. The base of the transistor 311 is also connected to the +15 V through a resistor 313. The emitter of the transistor 311 is connected to the +15 V through a resistor 314 and its collector is connected to the ground through a resistor 315. A capacitor 316 is connected in parallel with this resistor 315 so as to constitute two supply terminals of the aforementioned voltmeter 292.

As mentioned before, the initiation of the measurement of the damping of the oscillations is effected by means of the push-button 35 which may be, for example, disposed on the front side of a control box. A ground is applied to the base of the transistor 275 so as to permit supplying the relay 282. The switch 291 controlled by this relay 282 then moves to its second position so as to send the ORDER 2 signal to a plurality of circuits of the device and ensure the initiation of the measurement of the damping.

Figure 10:
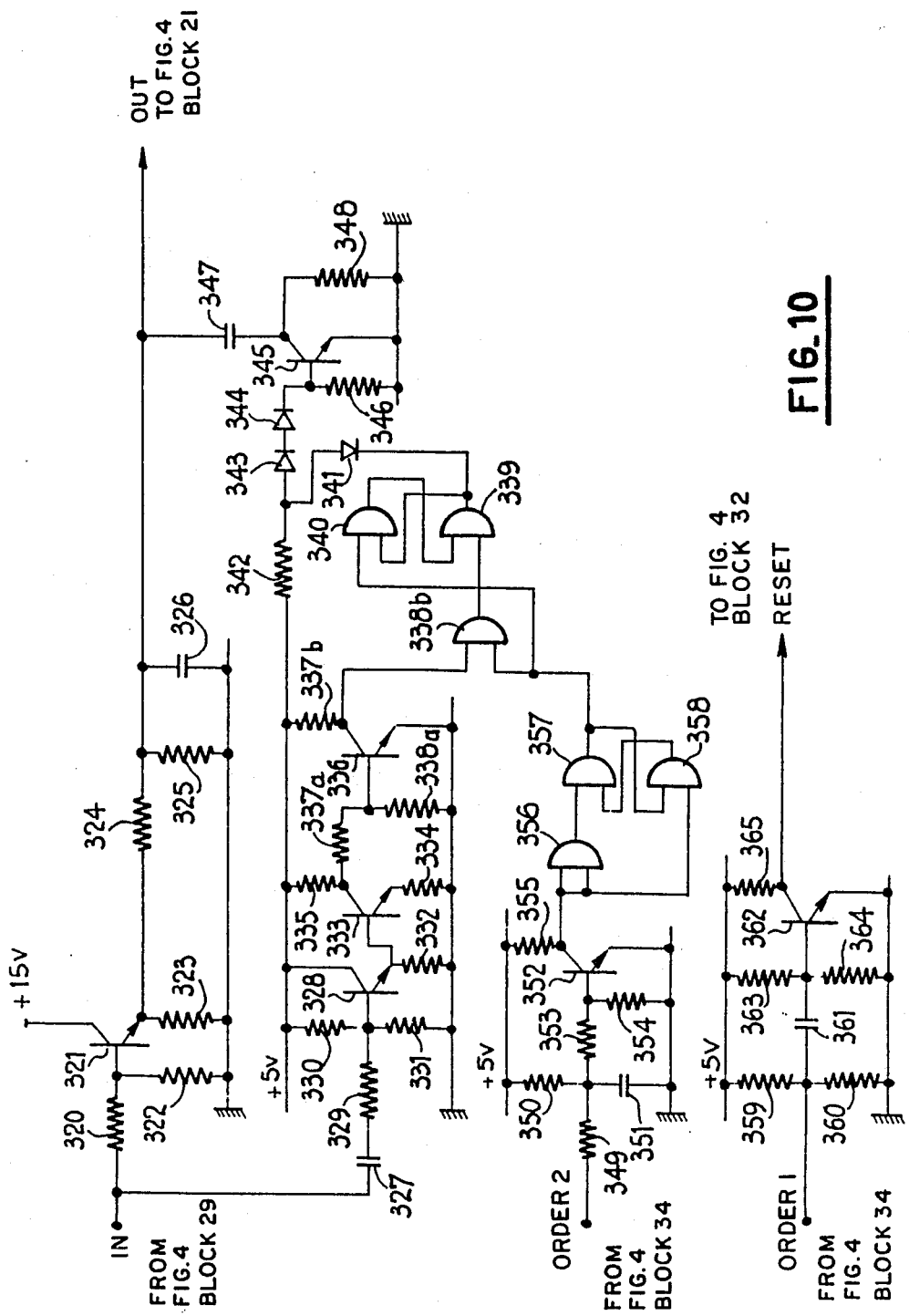
FIG. 10 is a diagram of a logic control circuit for the power amplifier and for resetting a damping counter which is part of the construction of a device according to the invention.

The ORDER signal delivered by the switch 291 in its position of rest is intended for the resetting of a damping counter which will be described in more detail hereinafter. For this purpose, these various signals delivered by this control circuit are applied to the logic means 30 for controlling the power amplifier and resetting the damping counter. These means 30 may be, for example, constituted as shown in FIG. 10.

This circuit receives the output of the pre-amplifying and filtering means 29 which is applied to a terminal of a resistor 320 whose other terminal is connected to the base of an NPN transistor 321. The base of this transistor 321 is also connected to the ground through a resistor 322 and its collector is connected to the +15V. The emitter of this transistor 320 is connected to the ground through a resistor 323 and to a terminal of a resistor 324 whose other terminal is connected to the ground through a resistor 325 and a capacitor 326 connected in parallel. This terminal of the resistor 324 is adapted to apply an output signal OUT to the power amplifier 21 supplying the primary winding. The output signal of the pre-amplifying and filtering means 29 is also applied to a terminal of a capacitor 327 whose other terminal is connected to the base of an NPN transistor 328 through a resistor 329. The base of this transistor 328 is also connected to the +5 V through a resistor 330 and to the ground through a resistor 331. The collector of this transistor 328 is connected to the +5 V. Its emitter is connected to the ground through a resistor 332 and to the base of an NPN transistor 333. The emitter of this transistor 333 is connected to the ground through a resistor 334 and its collector is connected to the +5 V through a resistor 335. The collector of the transistor 333 is also connected to the base of an NPN transistor 336 through a resistor 337a. The base of this transistor 336 is also connected to the ground through a resistor 338a. The emitter of the transistor 336 is connected to the ground. Its collector is connected on one hand to the +5 V through a resistor 337b and to an input terminal of an AND gate 338b. The output of this AND gate 338b is connected to an input of an AND gate 339 whose output is connected to an input terminal of an AND gate 340. The output of the AND gate 340 is loop-connected to an input of the AND gate 339. The output of the AND gate 339 is also connected to the cathode of a diode 341 whose anode is connected to the +5 V through a resistor 342. This resistor 342 is also connected to two diodes 343 and 344 connected in series and connected to the base of an NPN transistor 345. The base of this transistor 345 is also connected to the ground through a resistor 346. The emitter of this transistor 345 is connected to the ground and its collector is connected on one hand through a capacitor 347 to the output OUT of the circuit for the power amplifier 21 and constituted by the common terminal of the resistors 324 and 325 and of the capacitor 326 and, on the other hand, to the ground through a resistor 348.

This logic circuit also receives the ORDER 1 signal and ORDER 2 signal delivered by the previously-described control circuit. the order 2 signal is applied to a terminal of a resistor 349 whose other terminal is connected to the +5 V through a resistor 350 and to the ground through a capacitor 351. This resistor is also connected to the base of an NPN transistor 352 through a resistor 353. The base of this transistor 352 is connected to the ground through a resistor 354. The emitter of this transistor is also connected to the ground. Its collector is connected to the +5 V through a resistor 355. This collector is also connected to the two inputs of an AND gate 356 whose output is connected to an input of an AND gate 357. The collector of the transistor 352 is also connected to an input of an AND gate 358 whose output is loop-connected to an input of the AND gate 357. the output of this AND gate 357 is loop-connected to an input of the AND gate 358. This output of the AND gate 357 is also connected to an input of the AND gate 338b and of the AND gate 340.

The ORDER 1 signal is applied to a resistor 359 connected to the +5 V, to a resistor 360 connected to the ground and to a terminal of a capacitor 361 whose other terminal is connected to the base of an NPN transistor 362. This base of the transistor 362 is also connected to the +5 V through a resistor 363 and to the ground through a resistor 364. The emitter of this transistor 362 is connected to the ground. Its collector is connected to the +5 V through a resistor 365 and constitutes the output delivering a resetting signal for the damping counter.

The circuit just described with reference to FIG. 10 permits the cutting off of the supply of the primary winding by cutting off the power amplifying means 21 described with reference to FIG. 4. The transistor 345 is used for this purpose as a circuit breaker. This transistor connects to the ground the voltage which is applied to the power amplifier when the ORDER 2 signal is received from the control circuit in response to the actuation of the test push-button 35. The cutting off of this supply occurs when the applied voltage passes to zero owing to a circuit shaped by bistable elements constituted by the AND gates 356, 357, 358, 338b, 339, 340 and the transistors 328, 333, 336.

This circuit also receives the ORDER 1 signal for producing by means of the transistor 362 a signal for resetting the damping counter.

Figure 11:
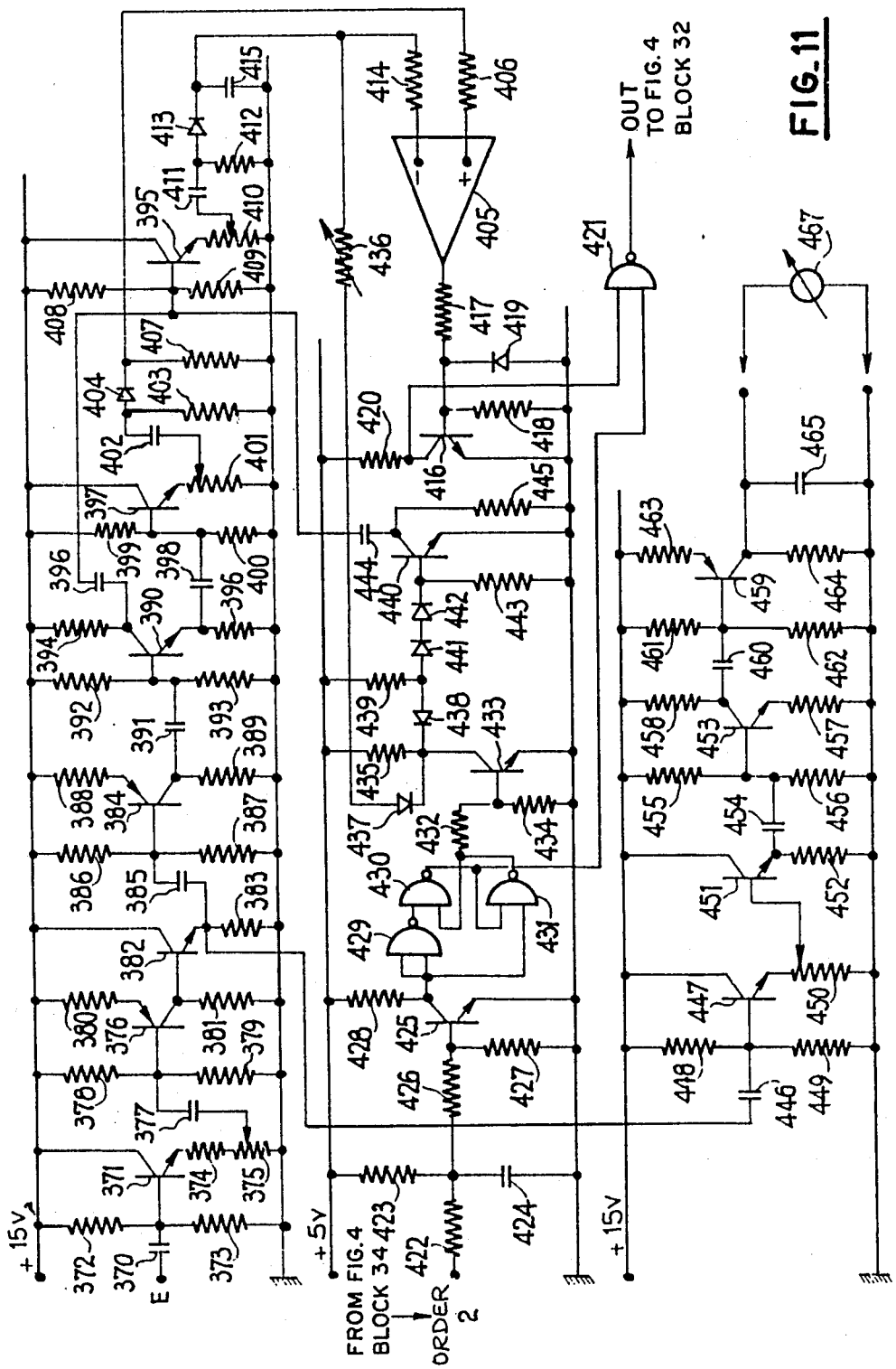
FIG. 11 is a diagram of means for cutting off the supply of the power amplifier which is part of the construction of a device according to the invention.

The means 33 for shaping the output signal of the secondary winding for the counting may be in the form of the circuit shown in FIG. 11. The signal coming from the various voltage regulating means, pre-amplifying and filtering means such as those described before, is applied to a terminal of a capacitor 370 whose other terminal is connected to the base of an NPN transistor 371. The base of this transistor 371 is also connected to the +15 V through a resistor 372 and to the ground through a resistor 373. The collector of this transistor is connected to the +15 V and its emitter is connected to the ground through a resistor 374 and a potentiometer 375 whose slider is connected to the base of a PNP transistor 376 through a capacitor 377. The base of this transistor 376 is also connected to the +15 V through a resistor 378 and to the ground through a resistor 379. The emitter of this transistor 376 is connected to the +15 V through a resistor 380 and the collector of this transistor is connected to the ground through a resistor 381. This collector is also connected to the base of an NPN transistor 382 whose collector is connected to the +15 V. The emitter of this transistor is connected to the ground through a resistor 383 and to the base of a PNP transistor 384 through a capacitor 385. The base of this transistor 384 is also connected to the +15 V through a resistor 386 and to the ground through a resistor 387. The emitter of this transistor 384 is connected to the +15 V through a resistor 388 and its collector is connected to the ground through a resistor 389. This collector is also connected to the base of an NPN transistor 390 through a capacitor 391. This base is also connected to the +15 V through a resistor 392 and to the ground through a resistor 393. The collector of the transistor 390 is connected to the +15 V through a resistor 394 and to the base of an NPN transistor 395 through a capacitor 396. The emitter of the transistor 390 is connected to the ground through a resistor 396 and to the base of an NPN transistor 397 through a capacitor 398.

The base of this transistor 397 is connected to the +15 V through a resistor 399 and to the ground through a resistor 400. The collector of the transistor 397 is connected to the +15 V and its emitter is connected to the ground through a potentiometer 401. The slider of this potentiometer is connected to a terminal of capacitor 402 whose other terminal is connected to the ground through a resistor 403 and to the diode 404 connected to the non-inverting input of an operational amplifier 405 through a resistor 406. This non-inverting input is also connected to the ground through a resistor 407.

The base of the transistor 395 is connected to the +15 V through a resistor 408 and to the ground through a resistor 409. The collector of this transistor is connected to the +15 V and its emitter is connected to the ground through a potentiometer 410. The slider of this potentiometer is connected to a terminal of a capacitor 411 whose other terminal is connected to the ground through a resistor 412 and to a diode 413. This diode is also connected to the inverting input of the operational amplifier 405 through a resistor 414. This inverting input is also connected to the ground through a capacitor 415. The output of this operational amplifier is connected to the base of an NPN transistor 416 through a resistor 417. The base of this transistor 416 is connected to the ground through a resistor 418 to the terminals of which is connected a diode 419. The collector of the transistor 416 is connected to the +15 V through a resistor 420. This collector is also connected to an input of an AND gate 421. The emitter of the transistor 416 is connected to the ground.

This circuit also receives the ORDER 2 signal which is applied to a terminal of a resistor 422. The other terminal of this resistor 422 is connected to the +5V through a resistor 423, to the ground through a capacitor 424 and to the base of an NPN transistor 425 through a resistor 426. This base of the transistor 425 is also connected to the ground through a resistor 427. The emitter of this transistor is connected to the ground. This collector is connected to the +5V through a resistor 428 and to the inputs of a NAND gate 431. The output of the NAND gate 430 is loop-connected to one of the inputs of the NAND gate 431 and the output of the latter is loop-connected to the other input of the NAND gate 430. This output of the gate 431 is also connected to a terminal of a resistor 432 whose other terminal is connected to the base of an NPN transistor 433 and to the ground through a resistor 434. The emitter of the transistor 433 is connected to the ground. Its collector is connected to the +5V through a resistor 435 and to a terminal of an adjustable resistor 436 through a diode 437 inversely connected. The other terminal of the adjustable resistor 436 is connected to the common point between the diode 413, the capacitor 415 and the resistor 414 connected to the inverting input of the operational amplifier 405.

The collector of the transistor 433 is also connected to the cathode of a diode 438 whose anode is connected to the +5V through a resistor 439 and to the base of an NPN transistor 440 through two diodes 441 and 442 connected in series with said resistor 439. The base of the transistor 440 is also connected to the ground through a resistor 443. The emitter of the latter is connected to the ground. Its collector is connected through a capacitor 444 to the base of the transistor 395 and through a resistor 445 to the ground. The other input of the NAND gate 421 is connected to the output of the NAND gate 430.

The output OUT of this NAND gate 421 constitutes the output for delivering the signal which is applied to the counting and display means 32.

The emitter of the transistor 382 is also connected to a terminal of a capacitor 446 whose other terminal is connected to the base of an NPN transistor 447. This base is connected to the +15V through a resistor 448 and to the ground through a resistor 449. The collector of the transistor 447 is connected to the +15V and its emitter is connected to the ground through a potentiometer 450. The slider of this potentiometer is connected to the base of an NPN transistor 451 whose collector is connected to the +15V. The emitter of this transistor is connected to the ground through a resistor 452 and to the base of an NPN transistor 453 through a capacitor 454. The base of this transistor is also connected to the +15V through a resistor 455 and to the ground through a resistor 456. The emitter of the transistor 453 is connected to the ground through a resistor 457 and its collector is connected to the +15V through a resistor 458. This collector is also connected to the base of a PNP transistor 459 through a capacitor 460. This base is also connected to the +15V through a resistor 461 and to the ground through a resistor 462. The emitter of the transistor 459 is connected to the +15V through a resistor 463 and its collector is connected to the ground through a resistor 464. A capacitor 465 is connected in parallel to the terminals of this resistor 465 and a device 467 for reading off the counting voltage is connected in parallel to the terminals of this capacitor.

When the damping test order is given, the primary winding 5 is no longer supplied with current as mentioned before. The oscillation of the specimen then changes from the self-sustaining conditions by magnetostriction to conditions of damped oscillations. The output voltage of the secondary winding then decreases from its initial value Vo and tends toward 0. The counting of the pulses which serve to determine the internal friction of the specimen is then effected during a period of time $t = t_1 - t_0$, i.e. during the interval of time during which the amplitude of the voltage at the terminals of the secondary winding changes from its initial value Vo to $\alpha$Vo with for example $\alpha = 0.54$. The circuit just described permits the determination of this time t and the shaping of the detected pulses to permit the counting thereof. The input signal coming from the various means described before, is oriented from the transistor 390 toward two other parts of the circuit:

(1) Toward the transistor 395 for a detection by means of the diode 413 and an integration by means of the capacitor 415. The voltage at the terminals of the capacitor 415 then represents the value Vo. Note that the value of the voltage at the terminals of the capacitor 415 may be considered to be constant during the time t taken by the measurement of the damping. Indeed, the time constant of this circuit is so calculated as not to disturb the measurement for example with a time constant $\tau = RC \geqq 60t$, C being constituted by the value of the capacitor 415, for example 1 $\mu$F, and R being constituted by the value of the resistor 414 connected to the inverting input of the operational amplifier 405 and having for example the value of 240K$\Omega$.

(2) Toward the transistor 397 for a detection by means of the diode 404. The signal delivered then represents V (t), i.e. the image of the voltage coming from the secondary winding with respect to time. The signals V (t) and Vo are then set to the comparison means constituted by the operational amplifier 405 which delivers pulses as long as the value V (t) is greater than Vo.

These pulses are then levelled by the transistor 416 and then sent to the counting circuit through the NAND gate 421.

The signal delivered by the bistable element constituted by the NAND gates 429, 430 and 431 and the transistor 433 has two functions:

(1) Short-circuit the input of the transistor 395 so that the value $\alpha$ Vo is not disturbed by any parasite during the time T.

(2) Modify the value of the resistor connected in parallel with the capacitor 415. Indeed, under conditions of sustained oscillations, the amplitude of the voltage V (t) has a certain number of variations which the value $\alpha$ Vo must follow. Indeed, the time constant must be low under self-sustaining conditions in order to follow the evolutions of V (t) and high under free conditions relative to t.

Figure 12:
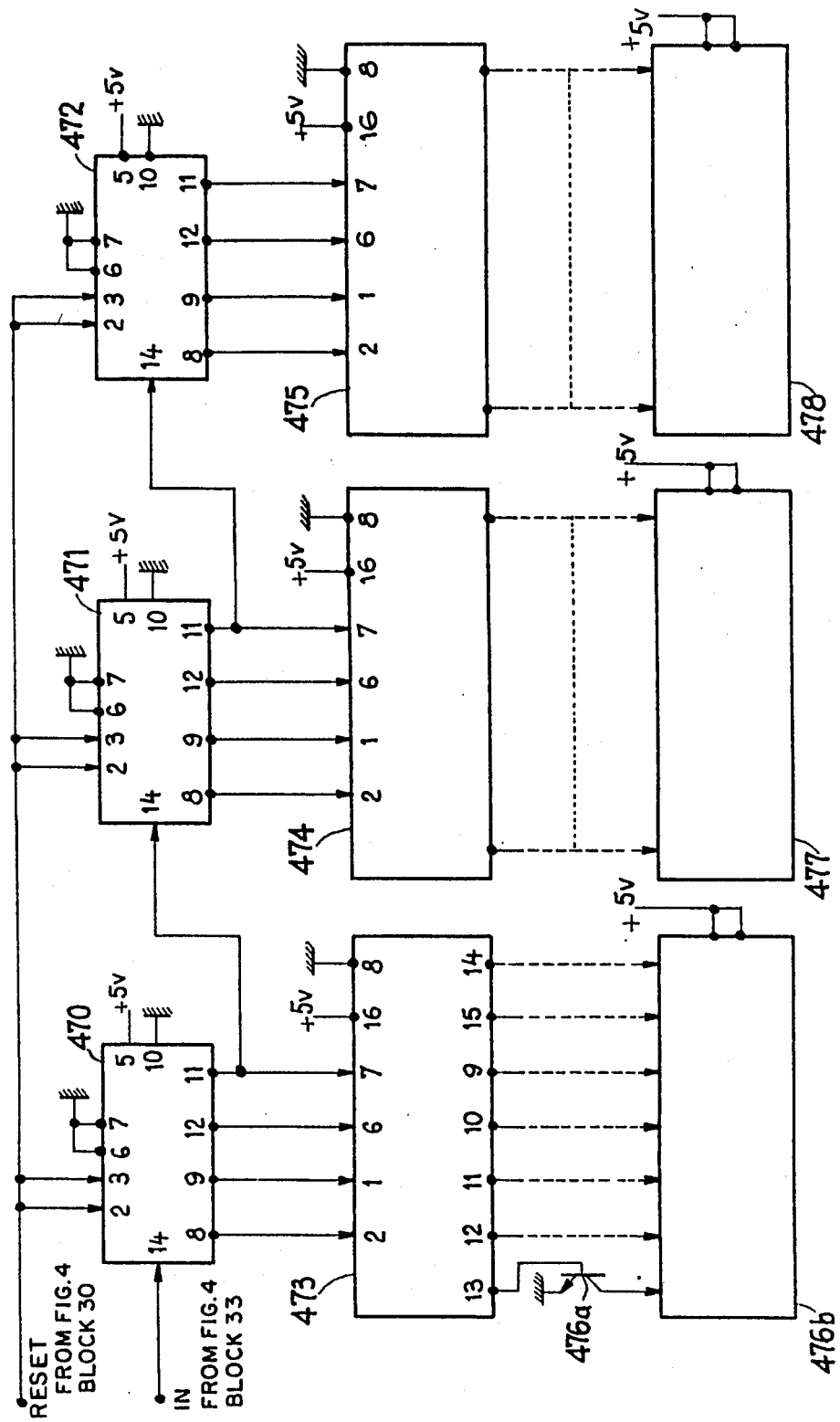
FIG. 12 is a diagram of means for counting and displaying the oscillations which is part of the construction of a device according to the invention.

The pulses delivered by this circuit are then counted by the counting and display means 32 which may be constituted for example by a circuit such as that shown in FIG. 12. The pulses are for example applied to a series of three decimal counters 470, 471 and 472, for example of the type 2N 7490. The counter 472 receives at its input terminal 14 the signal coming from the shaping means 33 and its output terminal 11 is connected to the input terminal 14 of the counter 471. The output 11 of this counter 471 is also connected to the input 14 of the counter 472. The terminals 2 and 3 of the counters 470, 471 and 472 receive the resetting signal delivered by the logic means 30. The terminals 6 and 7 of each counter are connected to the ground, the terminals 5 are connected to the +5V supply, the terminals 10 are connected to the ground and the terminals 8, 9, 12 and 11 of the counters 470, 471 and 472 are respectively connected to decoders 473, 474 and 475.

These decoders are for example of the type N 7448A and the output terminals of the counters are connected to the terminals 1, 2, 6, 7 of these decoders. The terminal 16 of the decoders is connected to the +5 V and the terminal 8 is connected to the ground. The output terminals 9, 10, 11, 12, 13, 14, 15 of these decoders are each connected to the base of an NPN transistor, for example 476a, whose emitter is connected to the ground and whose collector is connected to an input of a display having seven segments 476b, 477 and 478 whereby it is possible to display or read out the number of damped oscillations in units, tens and hundreds respectively.

Figure 13:
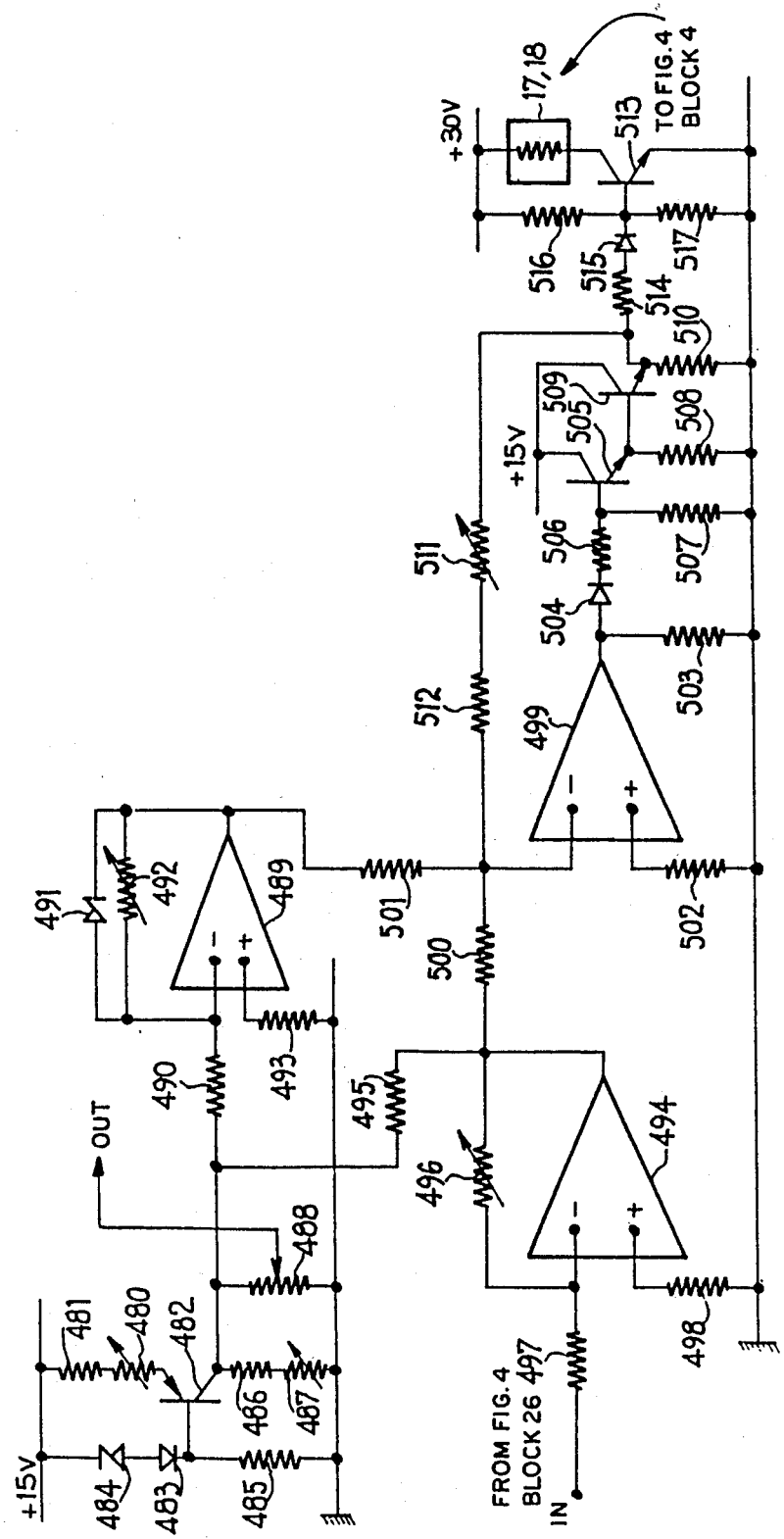
FIG. 13 is a diagram of means for regulating the temperature of the measuring enclosure which is part of the construction of a device according to the invention.

The device further comprises means 39 for regulating the temperature of the cell in which the specimen is located. These means are formed by two temperature indicators of the type PEN manufactured by the firm CHAUVIN-ARNOUX, two thermocouples 15 and 16 which were mentioned with respect to FIG. 3, a power supply and means 39 for regulating the temperature which maintain the temperature of the cell for example at 185° C.±1° C. These regulating means are formed for example by a circuit, such as shown in FIG. 13. An adjustable set in temperature is delivered by a current generator comprising an adjustable resistor 480 whose first terminal is connected to the +15 V through a resistor 481 and whose other terminal is connected to the emitter of a PNP transistor 482. The base of this transistor 482 is connected to the +15 V through a diode 483 and a Zener diode 484 connected in series. This base is also connected to the ground through a resistor 485. The collector of the transistor 482 is connected to the ground through a resistor 486 and an adjustable resistor 487. This collector is also connected to a terminal of a potentiometer 488 whose other terminal is connected to the ground and whose slider is connected to one of the temperature indicators so as to display the set temperature. The collector of the transistor 482 is also connected to an inverting input of an operational amplifier 489 through a resistor 490. The output of this operational amplifier 489 is loop-connected to its inverting input through a Zener diode 491 and an adjustable resistor 492. The non-inverting input of this operational amplifier 489 is connected to the ground through a resistor 493. The collector of the transistor 482 is also connected to the output of an operational amplifier 494 through a resistor 495. This output of the operational amplifier 494 is also loop-connected to its inverting input through an adjustable resistor 496. This inverting input is also connected to a terminal of a resistor 497 whose other terminal receives information coming from the other temperature indicator and receives a signal which represents the real temperature inside the cell.

The non-inverting input of the operational amplifier 494 is connected to the ground through a resistor 498. The output of the operational amplifier 494 is connected to the inverting input of an operational amplifier 499 through a resistor 500. The output of the operational amplifier 499 is also connected to this inverting input of the operational amplifier 499 through a resistor 501. The non-inverting input of this operational amplifier 499 is connected to the ground through a resistor 502. The output of the operational amplifier 499 is connected to the ground through a resistor 503 and to the anode of a diode 504 whose cathode is connected to the base of an NPN transistor 505 through a resistor 506.

The base of this transistor 505 is connected to the ground through a resistor 507 and its collector is connected to the +15 V. The emitter of this transistor 505 is connected to the ground through a resistor 508 and to the base of an NPN transistor 509 whose collector is also connected to the +15 V. The emitter of this transistor 509 is connected to the ground through a resistor 510 and to the inverting input of the operational amplifier 499 through an adjustable resistor 511 and a resistor 512. The emitter of the transistor 509 is also connected to the base of a power transistor NPN 513 through a resistor 514 and a diode 515. The base of this transistor 513 is connected to the +30 V supply through a resistor 516 and to the ground through a resistor 517.

The emitter of this transistor 513 is connected to the ground and its collector is connected to the heating resistors 17, 18 of the heating means described with reference to FIG. 3.

The temperature inside the cell is therefore compared to the set temperature delivered by the current generator constituted by the transistor 482 and the associated components and the result of this comparison pilots the power transistor 513 which serves to supply power to the heating resistors of the heating means for maintaining the temperature at the set value.

The various supply means of the elements just described are constituted by known stabilized supplies and will not be described in more detail.

It will be understood that the calculating means may be connected to the counting means so as to directly calculate the coefficient of internal friction and, for example, the content of interstitial elements, from the number N of damped oscillations.

Also, the specimen is made to oscillate. In this respect, U.S. Pat. No. 3,706,026 discloses an apparatus for determining the frequencies of resonance of a specimen of magnetostrictive material in which said specimen is placed inside three windings similar to those employed for vibrating the specimen in the device according to the invention.

What is claimed is:

1. A process for determining the coefficient of internal friction of an elongate specimen of ferromagnetic material, in particular for determining the content of interstitial elements of said material, said process comprising exciting the specimen electromagnetically so as to impart thereto longitudinal oscillations, cutting off the excitation, electromagnetically measuring an attenuation of said oscillations by counting the number N of damped oscillations whose amplitude is equal to at least the initial amplitude of said oscillations multiplied by a coefficient $\alpha$, wherein the number N of damped oscillations is used to compute the coefficient of internal friction of the specimen.

2. A process according to claim 1, comprising determining the coefficient $Q^{-1}$ of internal friction of the specimen from the relation:

$$Q^{-1} = (L_n \, 1/\alpha) \, \pi N$$

3. A process according to claim 1, wherein $\alpha$ is equal to 0.54.

4. A process according to claim 1, comprising varying the temperature of the specimen.

5. A process according to claim 1, comprising maintaining the specimen at a fixed temperature.

6. A process according to claim 1, comprising determining the frequency f of the longitudinal oscillations imparted to the specimen from the relation;

$$f = \sqrt{E/4 \, dl^2}$$

in which E designates the modulus of elasticity of the tested ferromagnetic material, l is the length of the specimen, and d the density of the tested material.

7. A device for determining the coefficient of internal friction of an elongate specimen of ferromagnetic material, in particular for determining the content of interstitial elements of said material, said device comprising excitation means for electromagnetically imparting longitudinal oscillations to the specimen, means for cutting off the excitation means, means for electromagnetically detecting and counting damped oscillations whose amplitude is equal to at least the initial amplitude of the oscillations multiplied by a coefficient $\alpha$, wherein detecting and counting of said damped oscillations occur after said cutting of said excitation and wherein the damped oscillations can be used to compute said coefficient of internal friction.

8. A device according to claim 7, wherein said exitation means comprise three coaxial cylindrical windings surrounding said specimen, comprising a primary winding disposed around an end portion of the specimen and a first supply means connected to said primary winding for causing said specimen to oscillate by magnetostriction in the longitudinal direction, a polarization winding disposed around a central portion of the specimen and a second supply means connected to said polarization winding for ensuring a magnetic polarization of the specimen, and a secondary winding disposed around an opposite end portion of the specimen and means connected to said secondary winding for detecting and counting the damped oscillations.

9. A device according to claim 7, wherein said means for cutting off the excitation comprise means for cutting off said supply means of said primary winding.

10. A device according to claim 7, wherein said means for detecting the damped oscillations comprise comparison means having a first input and a second input, signal processing means connecting said first input to an output of said secondary winding and means for delivering a reference signal connected to said second input.

11. A device according to claim 10, wherein said comparison means comprise an operational amplifier.

12. A device according to claim 10, wherein the means delivering a reference signal comprise a resistor and a capacitor connected to said input of the comparison means for applying thereto a voltage equal to the initial value of the amplitude of the oscillations multiplied by the coefficient $\alpha$.

13. A device according to claim 10, wherein the processing means comprise regulating means, filtering and amplifying means, and means for shaping the output signals of the secondary winding.

14. A device according to claim 7, comprising means for displaying the number N of damped oscillations.

15. A device according to claim 7, comprising a measuring cell containing said windings and said specimen, heating means connected to said cell, and means for controlling and regulating the temperature in said cell.

16. A device according to claim 15, wherein said heating means comprise a plurality of means for blowing air into said cell and a pipe opening onto one of the ends of said specimen connecting at least one of said blowing means to said cell.

17. A device according to claim 16, wherein said heating means comprise heating resistors connected to the regulating means so as to regulate the temperature inside said cell.

18. A device according to claim 17, wherein said regulating means comprise a power transistor connected to the heating resistors in such manner as to control their supply for regulating the temperature in said cell.

19. A device according to claim 7, comprising insulating supports in said windings, on which supports said specimen is placed.

20. A device according to claim 19, wherein said supports are of Teflon.

21. An application of a process in a study of the kinetics of precipitation of an interstitial element in steel, said process comprising exciting the specimen electromagnetically so as to impart thereto longitudinal oscillations, cutting off the excitation, measuring an attenuation of said oscillations by counting the number N of damped oscillations whose amplitude is equal to at least the initial amplitude of said oscillations multiplied by a coefficient $\alpha$, and determining the internal coefficient of friction of the specimen from said number of oscillations, said process further comprising maintaining the temperature of the specimen at a given value corresponding to the Snoek peak for the considered interstitial element, measuring the variation of the height of the Snoek peak as a function of time and deducting the kinetics of precipitation from the kinetics of the lowering of said peak.

22. An application of the process according to claim 21 wherein the interstitial element is carbon.

23. An application of the process according to claim 21, wherein the interstitial element is nitrogen.

* * * * *

UNITED STATES PATENT AND TRADEMARK OFFICE
CERTIFICATE OF CORRECTION

PATENT NO. : 4,852,406

DATED : August 1, 1989

INVENTOR(S) : Oliver, et al

It is certified that error appears in the above-identified patent and that said Letters Patent is hereby corrected as shown below:

Title page, Item [19] change "Chrithian" to --Oliver--;

Title page, Item [75] change "Oliver Christian" to

--Christian Oliver--.

Signed and Sealed this

Seventeenth Day of July, 1990

Attest:

HARRY F. MANBECK, JR.

*Attesting Officer*      *Commissioner of Patents and Trademarks*